United States Patent [19]

Sting et al.

[11] Patent Number: 4,653,880
[45] Date of Patent: Mar. 31, 1987

[54] REFLECTIVE BEAM SPLITTING OBJECTIVE

[75] Inventors: Donald W. Sting, New Canaan; Robert G. Messerschmidt, Westport, both of Conn.

[73] Assignee: Spectra-Tech Inc., Stamford, Conn.

[21] Appl. No.: 707,231

[22] Filed: Mar. 1, 1985

[51] Int. Cl.⁴ .......................... G02B 17/06; G02B 5/10
[52] U.S. Cl. ..................................... 350/620; 350/622
[58] Field of Search .............. 350/172, 171, 169, 620, 350/619, 525, 523, 505, 504, 442, 445, 511, 622, 623, 624; 356/435

[56] References Cited

U.S. PATENT DOCUMENTS

| | | | |
|---|---|---|---|
| 2,478,762 | 8/1949 | Johnson | 88/39 |
| 2,628,529 | 2/1953 | Braymer | 350/442 |
| 2,743,646 | 5/1956 | Strong | 88/14 |
| 3,010,358 | 11/1961 | Siegler | 38/14 |
| 3,251,219 | 5/1966 | Hertz et al. | 73/67.7 |
| 3,411,852 | 11/1968 | Marinozzi | 350/622 |
| 3,521,943 | 7/1970 | Kelderman | 350/162 |
| 3,858,046 | 12/1974 | Cubalchini | 250/353 |
| 3,961,179 | 6/1976 | Kuffer | 250/203 R |
| 3,968,362 | 7/1976 | Mocker | |
| 4,395,095 | 7/1983 | Horton | 350/505 |
| 4,594,509 | 6/1986 | Simon | 250/338 |

FOREIGN PATENT DOCUMENTS

| | | |
|---|---|---|
| 0116321 | 1/1984 | European Pat. Off. . |
| 3208706 | 3/1982 | Fed. Rep. of Germany . |
| 359783 | 1/1962 | Switzerland . |
| 402445 | 5/1966 | Switzerland ........................ 350/442 |
| 1095123 | 5/1984 | U.S.S.R. ............................... 350/620 |

OTHER PUBLICATIONS

K. P. Norris, "A Reflecting Microscope for Infra-Red Absorption Measurements", Aug. 1954, Journal of Scientific Instruments, vol. 31, pp. 284–287, London, GB.

*Primary Examiner*—Jon W. Henry
*Attorney, Agent, or Firm*—Bacon & Thomas

[57] ABSTRACT

A reflecting beam splitting objective employing only three mirrors obtains a high reflective efficiency. In one embodiment, the objective contains a small intercepting mirror between primary and secondary mirrors of a Cassegrain mirror arrangement. The position of the intercepting mirror is determined so that the mirror receives an input beam and directs that beam onto a first portion of the secondary mirror without vignetting the beam when it is reflected from the secondary mirror to a first portion of the primary mirror or by cutting off part of the image transmitted from the second portion of the secondary mirror to a focus behind the primary mirror. The objective may use all energy that is input into the objective to image a sample. The objective has demonstrated particular utility in the field of infrared spectroscopy of small samples.

8 Claims, 4 Drawing Figures

U.S. Patent    Mar. 31, 1987    Sheet 1 of 2    4,653,880
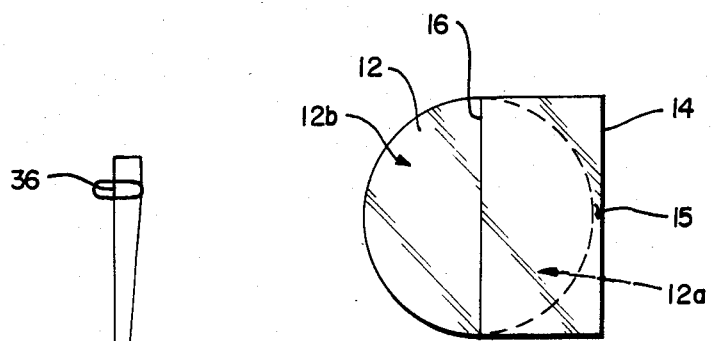
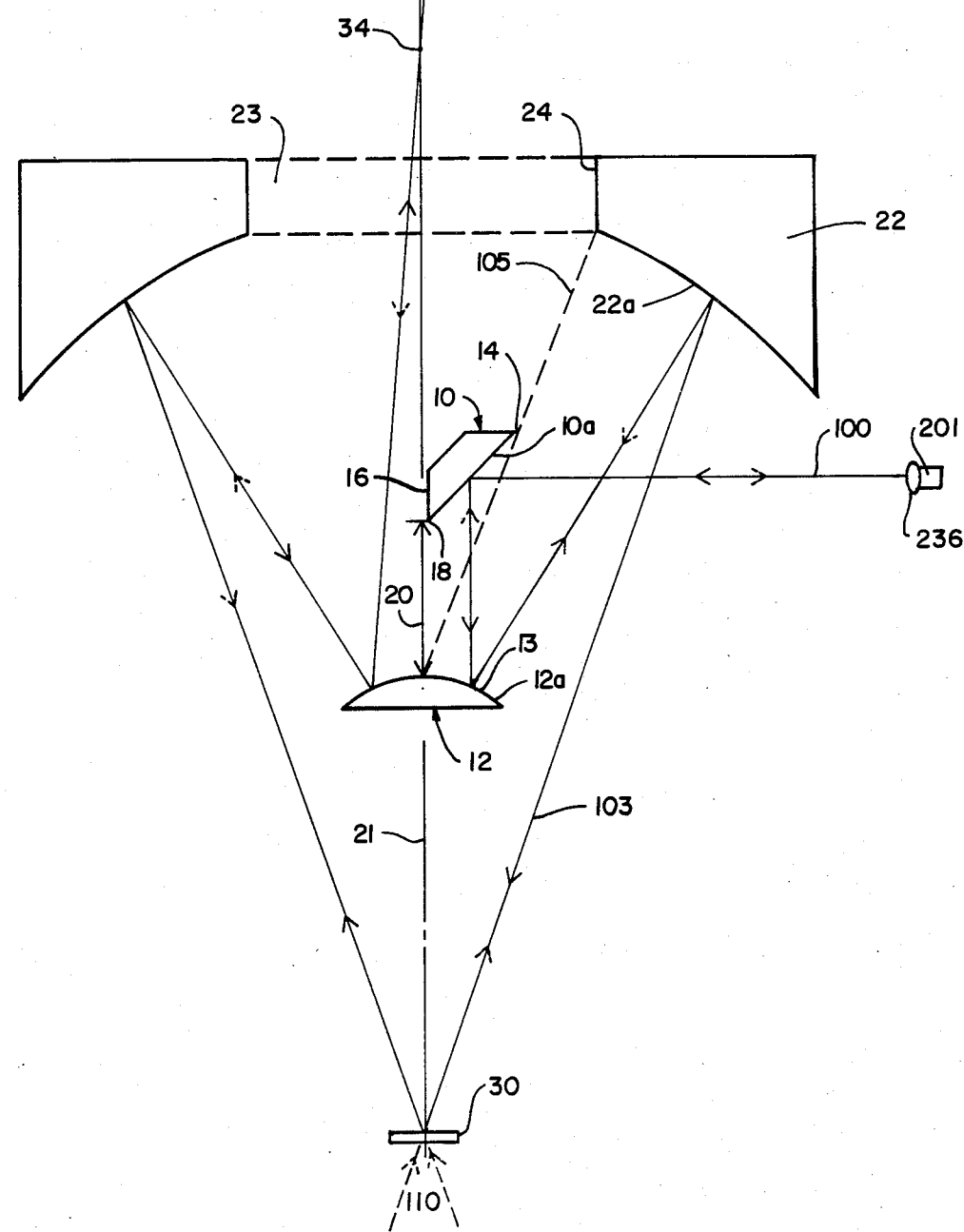

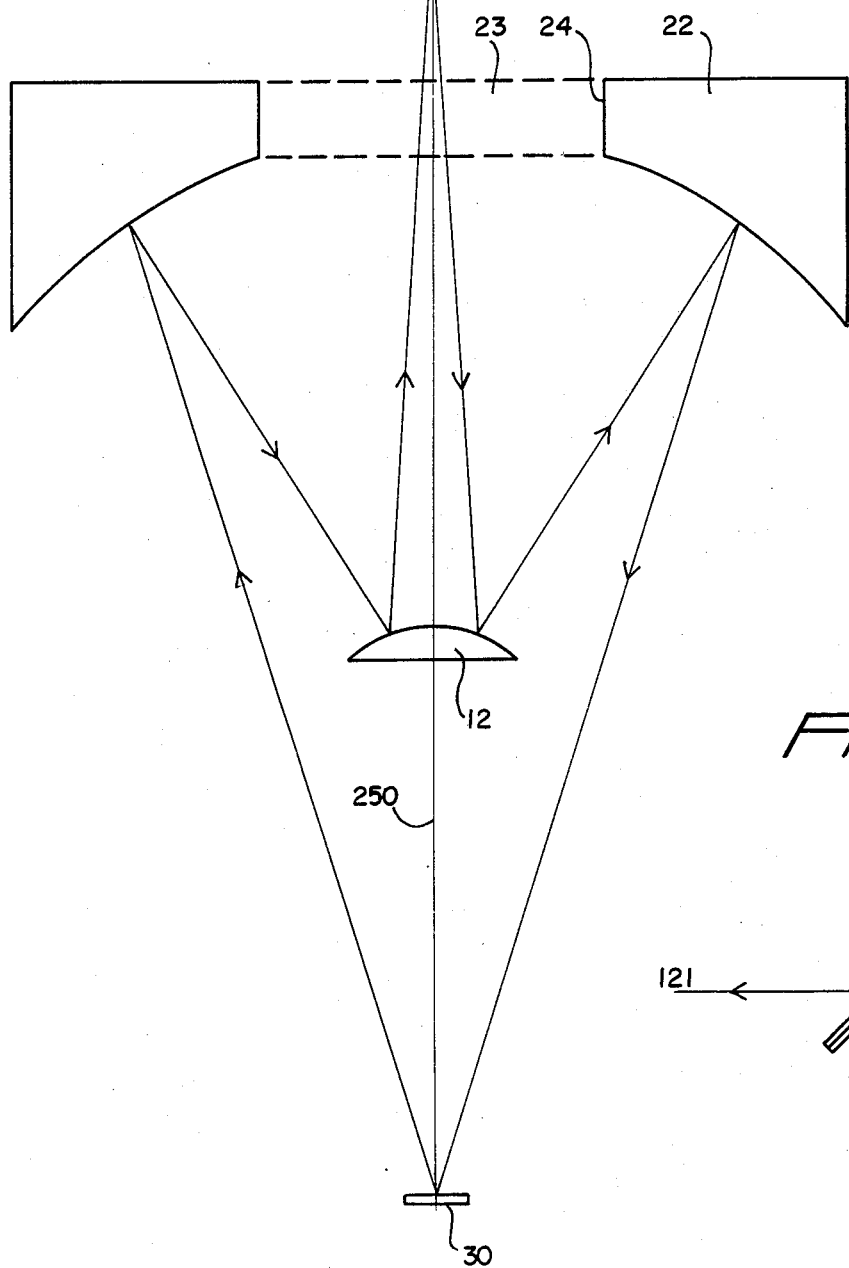

REFLECTIVE BEAM SPLITTING OBJECTIVE

FIELD OF THE INVENTION

This invention relates to a reflective beam splitting objective optical system for redirecting an energy beam that approaches the system at an angle to its optical axis or along the optical axis from either direction.

BACKGROUND OF THE INVENTION

It is often desirable or necessary to input an energy beam at an angle to an optical axis of a focusing objective system. The reflected beam from the sample often needs to be collected. Since reflection occurs according to Snell's Law, the reflected energy must be collected at the same angle to the sample as the angle of incidence. In visual imaging systems, to accurately view detail of a sample plane without distortion, the viewing system must be situated near normal to the sample. These conditions dictate that the incident and the reflected beams co-exist in space such that they are co-axial or near co-axial. In order to separate these beams, a beam splitter is used.

The most simple form of a beam splitter is a refractive beam splitter employing a partially reflective mirror that redirects the beam at substantially a right angle into a focusing system and then to the sample which then transmits part of a reflected beam back through the focusing system, beam splitter and onto a detector. A beam splitter of this type is theoretically limited to an efficiency of 25% because half of the input beam is lost on the initial reflection and half of the remaining beam is lost when the beam is transmitted through the beam splitter. This type of beam splitter also may introduce chromatic aberrations into the reflected beam. The refractive beam splitter, however, has the advantage of having a very simple construction.

Another means for splitting an input energy beam involves off-axis paraboloids, ellipsoids or spherical mirrors. These off-axis systems have means for directing the beam to a focusing mirror which focuses the beam onto a sample. Energy reflected from the sample is focused by a second mirror and directed to a detector through whatever optical arrangement is chosen. These systems have the disadvantage of introducing substantial distortions of the visual image, a phenomenon that is particularly troublesome at high magnifications. Off-axis systems are also not suitable for applications where it is desirable to mask part of the image being sent to the detector.

Finally, complex mirror arrangements may be created that illuminate the sample and recreate an undistorted image of the sample that may be used by a detector. These complex mirror arrangements, while producing an adequate optical path, involve considerable mechanical complexity and expense in manufacture. Moreover, complex systems involve complex problems of alignment of the optical components. Finally, these systems are generally not compact, making for a system that is cumbersome, complex and difficult to maintain in optical alignment.

Present beam splitters generally do not provide an economical and accurate method of redirecting an image beam at an angle to the optical axis of an infrared microscopic imaging system. This problem is particularly acute in connection with obtaining infrared spectra of extremely small size samples where it is necessary to mask the image received by the detector.

SUMMARY OF THE INVENTION

The present invention comprises a reflective beam splitting apparatus and process, wherein an energy beam intercepting mirror is positioned to divide the optical axis of a Cassegrain or similar reflecting objective. The intercepting mirror is positioned a sufficient distance from a secondary mirror so as not to vignette an energy beam directed from the secondary mirror to a primary mirror and sufficiently close to the secondary mirror so as not to unevenly attenuate an image formed behind the primary mirror. From the standpoint of a process, the invention comprises a procedure for directing an input energy beam at an angle substantially perpendicular to the optical axis of the system, wherein the beam is directed onto the axis of the system by an intercepting mirror which reflects the energy to a portion of the secondary mirror area then onto the primary mirror which directs the energy to the sample. Energy reflected off of the sample is focused and forms an image of the entire sample behind the primary mirror. The invention also comprises a procedure for inputting an energy beam substantially on the optical axis and using the intercepting mirror to divide the resulting image into a first component that the Cassegrain optics focuses on-axis to the system and a second component that is focused at an angle to the optical axis each component forming an image of the entire sample image.

In all embodiments, the present invention focuses all points on a sample located at the respective image planes, thus enabling visual inspection of a sample to determine from which areas energy may be received by one or more detectors. The invention has proven to have particular utility in the field of infrared microscopy.

BRIEF DESCRIPTION OF THE DRAWINGS

FIG. 1 shows a reflective beam splitting objective according to the present invention;

FIG. 2 is a top perspective of the intercepting mirror and secondary mirror shown in FIG. 1;

FIG. 3 is an illustration of a reflecting objective that is useful for understanding the present invention; and FIG. 4 shows a partially transmitting/partially reflecting beam splitter.

DETAILED DESCRIPTION OF A PREFERRED EMBODIMENT

Referring to FIG. 1, the optical arrangement constructed in accordance with a preferred embodiment of the present invention has an intercepting mirror 10 with a reflective surface 10a positioned above a secondary mirror 12 having a reflective surface 13. Positioned over a first portion 12a of secondary mirror 12 is an intercepting mirror 10 having a first edge 14 extending beyond an edge of secondary mirror 12 for example by a distance indicated by 15 in FIG. 2. A second side edge 16 of intercepting mirror 10 is aligned over secondary mirror 12 so as to form a great diameter on mirror 12 as shown in FIG. 2. The intercepting mirror 10 is positioned in between a primary mirror 22 having a reflective surface 22a and secondary mirror 12. A lower edge 18 of mirror 10 is separated from the uppermost surface of secondary mirror 12 by a distance 20. Mirror surfaces 13 and 22a are substantially concentric except for minor adjustments for aberrations.

The position of the intercepting mirror is determined by the following considerations. If the intercepting mirror is close to third image plane 36, the mirror attenuates part of the image; therefore, to maintain an evenly illuminated image on third image plane 36, intercepting mirror 10 should be as far from the image plane as possible. In the optical arrangement shown in FIG. 1, this design consideration, by itself, would ideally place the intercepting mirror as close as physically possible to secondary mirror 12. However, placing the intercepting mirror too close to the secondary mirror places first edge 14 of mirror 10 in the path of a portion of the energy reflected between first portion 12a of mirror 12 and the primary mirror 22 causing edge 14 to vignette the beam. Therefore, the distance 20 separating intercepting mirror 10 from secondary mirror 12 must permit a ray 105 to pass from the uppermost point on mirror 12 to the bore hole edge 24 of mirror 22 without being blocked by first edge 14 of mirror 10. Thus, mirror 10 should be positioned off axis to neither unevenly attenuate the image on image plane 36 or vignette ray 105. The most preferred position for mirror 10 has the lower edge 18 of mirror 10 separated by a distance 20 that is the smallest distance necessary to prevent edge 14 from vignetting ray 105.

As shown in FIG. 3, in an optical arrangement employing a Cassegrain arrangement of a primary and secondary mirror without the intercepting mirror, one-half of a symmetric input beam 200 would be directed along the optical axis 250 of the system to secondary mirror 12. The input beam would be focused by the Cassegrain optics onto second image plane 30 as in the present invention. The mirrors would image the sample back to the source at third image plane plane 36. However, one-half of the image must fall on the emitter 201 of beam 200. Therefore, employing a Cassegrain mirror arrangement without the intercepting mirror requires losing one-half of the image field. In contrast, the present invention employs intercepting mirror 10 to rotate the source of input energy so that the input beam is roughly perpendicular to the optical axis 21. The intercepting mirror directs the input beam from first image plane 236 to the secondary mirror from where the beam is reflected to the primary mirror which focuses the light to form an image at second image plane 30 on the sample which is in turn focused to an image behind focus 34 at third image plane 36 as shown in FIG. 1. The optical arrangement of the present invention does not require source 201 to block out half of the image of the sample at third image plane 36 because source 201 is no longer positioned on the sample plane. Therefore, all points of the sample are imaged on third image plane 36.

The present invention has the potential to obtain a 100% increase in efficiency over a conventional refractive beam splitter of the general type shown in FIG. 4. In FIG. 4, a symmetric input beam 120 falls on the refractive beam splitter 122. A part of the beam indicated by 121 passes through the refractive beam splitter and is lost from the system. Another part is reflected down to sample plane 130 through a reflecting objective 131. The energy reflected back from the sample through the reflecting objective again encounters beam splitter 122 which reflects part of the energy from the sample plane to the input source. At most only one quarter of the input energy may reach focus 34 if the refractive beam splitter 122 transmits and reflects exactly one-half of the incident energy. The efficiency of the system decreases if refractive beam splitter 122 reflects or transmits more than one-half of the incident energy. In practice, it has been found that a conventional refractive beam splitter may obtain efficiencies of only approximately 20% or less. This is especially true for beam splitters used with infrared energy beams. This level of efficiency is unacceptable for many applications.

The beam splitter of the present invention need lose only one-half of the energy contained in input beam 100. This energy is lost because secondary mirror 12 may reflect only one-half of a symmetrical beam; the other half of the beam must be lost. The efficiency of the system also depends on the reflectivity of the sample. If the sample at second image plane at second image plane 30 is perfectly reflective, i.e., a mirror, the efficiency of the system approaches 50%, i.e., all the energy input into the objective and reflectivity redirected by the intercepting mirror 10 reaches focus 34. If, however, the sample at second image plane 30 is diffusively reflective, i.e., reflecting the incident energy in a hemispherical pattern, one-half of the collected reflected energy is reflected along the input path and does not reach third image plane 34. Thus, in the worst case, the reflective beam splitting objective of the present invention obtains an efficiency of only 25% of the collectable energy, or an efficiency that is equal to the best possible efficiency obtainable with a conventional refractive beam splitter arrangement of the type shown in FIG. 4.

The reflective beam splitter apparatus of the present invention may have an input beam 110 focused at second image plane 30 along the optical axis. Energy passing through the second image plane fills primary mirror 22. Substantially half of the energy from mirror 22 is reflected from secondary mirror 12 to intercepting mirror 10 and focused off the optical axis 21 of the system at first image plane 231. Substantially half of the energy collected by the primary mirror reaches third image plane 34 on the optical axis of the system. Thus, operated in a transmissive mode, the optical arrangement of the present invention splits input beam 110 into two components and images each component. Each image of the beam splitter contains information from the entire second image plane 30 so long as intercepting mirror 10 is not close to third image plane plane 36 and edge 14 does not vignette ray 105. The closer intercepting mirror 10 comes to third image plane 36 the greater the uneven attenuation of the image on the side of the optical axis of mirror 10 caused by mirror 10. If edge 14 vignettes ray 105, a portion of the image of the sample at second image plane 30 reaching third image plane 36 is attenuated. Therefore, the same considerations apply for positioning mirror 10 as were described above.

The input energy beam also could be sourced at the third image plane 36 and reflect an image from the sample to first image plane 236, in reverse to that illustrated.

The optical arrangement according to the present invention also contemplates placing the intercepting mirror between the secondary and primary mirrors so as to make the reflective beam splitting objective an integral unit. This arrangement has proven to have particular utility for obtaining a stable aligned optical configuration. It has been found that the alignment of the optical component is particularly critical to obtaining a high efficiency when the intercepting mirror is at its minimum distance from the secondary mirror. The secondary mirror may be made of glass while the intercepting mirror and the primary mirror are preferably made of metal, e.g., stainless steel, which may be coated with aluminum. The stainless steel enables holes to be placed into the base of the mirror so as to provide known reference points for relating the surface of the mirror to the optical path and structural components. This mechanical assembly greatly simplifies initial optical alignment and serves to better maintain the optical alignment. Further, by placing the intercepting mirror between the primary and secondary mirrors, the reflecting beam splitting objective of the present invention has a smaller size than can be obtained by placing the intercepting mirror elsewhere, such as behind the primary mirror. Also, vignetting of ray 105 may be reduced by making first edge 14 as sharp as possible so that jagged edges do not protrude into the path of the ray.

A Cassegrain arrangement of the mirrors in the system produce an optimum reflecting objective. However, other lens arrangements could be used. A pure mirror arrangement, such as disclosed above, has particular utility for use in infrared spectroscopy. Other optical arrangements, such as a Maksutov optical arrangement, could be used.

The principles, preferred embodiments and modes of operation of the present invention have been described in the foregoing specification. The invention which is intended to be protected herein should not, however, be construed and limited to the particular forms described, as these are to be regarded as illustrative rather than restrictive. Variations and changes may be made by those skilled in the art without departing from the spirit of the invention. Accordingly, the foregoing detailed description should be considered exemplary in nature and not limiting to the scope and spirit of the invention set forth in the appended claims.

What is claimed is:

1. A reflective beam splitting objective for a microscope optical system, comprising:
   an optical axis for the system;
   a primary mirror on the optical axis, said primary mirror having a generally concave reflective surface including first and second portions;
   a secondary mirror on the optical axis, said secondary mirror having a generally convex reflective surface positioned so as to reflect an energy beam to or from the reflective surface of said primary mirror, said secondary mirror reflective surface including first and second portions;
   an intercepting mirror having a reflective surface positioned off the optical axis at a skew thereto so as to redirect energy to or from said first portion of said secondary mirror;
   said primary mirror, said secondary mirror and said intercepting mirror positioned to form first, second and third image planes for first, second and third images, respectively, said first image plane being located a finite distance off the optical axis at a skew thereto, said second image plane located on the optical axis a finite distance from the reflective surface of said primary mirror, said third image plane located on the optical axis a finite distance from the reflective surface of said secondary mirror;
   said intercepting mirror having minimum practical physical separation from the secondary mirror so as to intercept as little as possible radiant energy passing between the second image plane, the second portion of the primary mirror, the second portion of the secondary mirror and the third image plane; and
   said intercepting mirror being positioned sufficiently away from the secondary mirror along the optical axis so as not to block radiant energy forming said first and second images that passes between the first image plane, the first portions of said primary and second mirrors and the second image plane.

2. The optical system as claimed in claim 1, wherein:
   the reflective surface of the intercepting mirror is positioned between the primary and secondary mirrors; and
   said intercepting mirror being positioned close enough to the secondary mirror such that said reflective surface of said intercepting mirror is completely filled with all the radiant energy from the first portion of the secondary mirror which forms the second and third images and passes between the second image plane, the second portion of the primary and secondary mirrors and the third image plane;

3. The optical system as claimed in claim 1, wherein said first, second and third images are real images.

4. The optical system as claimed in claim 1, wherein said first and third images are virtual images and said second image is a real image.

5. The optical system as claimed in claim 1, wherein:
   said first and second portions of said primary mirror have equal reflective surface area; and
   said first and second portions of said secondary mirror have equal reflective surface area.

6. The optical system as claimed in claim 1, further comprising:
   means for receiving radiant energy at the first image plane from a source of radiant energy, said receiving means being positioned on the optical axis;
   means for positioning a sample on the optical axis at the second image plane; and
   means for directing the radiant energy from the third image plane to a detector, said directing means being positioned on the optical axis.

7. The optical system as claimed in claim 1, further comprising:
   means for receiving radiant energy at the second image plane from a source of radiant energy, said receiving means being positioned on the optical axis;
   means for positioning a sample on the optical axis at the second image plane; and
   means for directing the radiant energy from the second image plane to a detector, said directing means being positioned on the optical axis.

8. The optical system as claimed in claim 1, further comprising means for receiving radiant energy at said second image plane from a source of radiant energy, said receiving means being substantially on axis.

* * * * *

UNITED STATES PATENT AND TRADEMARK OFFICE
CERTIFICATE OF CORRECTION

PATENT NO. : 4,653,880

DATED : March 31, 1987

INVENTOR(S) : Donald W. STING ET AL.

It is certified that error appears in the above—identified patent and that said Letters Patent is hereby corrected as shown below:

Column 3, line 34, delete the first occurrence of "plane".

Column 4, line 14, delete the first occurrence of "at second image plane";

Column 4, line 44, delete the first occurrence of "plane";

Column 4, line 50, delete the second occurrence of "plane".

Column 6, line 15, delete "second mirrors" and insert --secondary mirrors--;

Column 6, line 28, delete ";" and insert --.--.

Signed and Sealed this

Ninth Day of February, 1988

Attest:

DONALD J. QUIGG

*Attesting Officer*   *Commissioner of Patents and Trademarks*

Disclaimer and Dedication

4,653,880—-Donald W. Sting, New Canaan; Robert C. Messerschmidt, Westport, both of Conn. REFLECTIVE BEAM SPLITTING OBJECTIVE. Patent dated March 31, 1987. Disclaimer and Dedication filed April 12, 2001, by the assignee, Spectra-Tech, Inc.

Hereby disclaims and dedicates to the Public all claims and entire term of said patent.
*(Official Gazette, June 12, 2001)*